United States Patent [19]

Marasco et al.

[11] Patent Number: 6,143,520

[45] Date of Patent: Nov. 7, 2000

[54] EXPRESSION VECTORS AND METHODS OF USE

[75] Inventors: Wayne A. Marasco, Wellesley; Jennifer Richardson, Boston, both of Mass.; Maria Cristina Parolin, Padua, Italy; Joseph G. Sodroski, Medford, Mass.

[73] Assignee: Dana-Farber Cancer Institute, Inc., Boston, Mass.

[21] Appl. No.: 09/060,659

[22] Filed: Apr. 15, 1998

Related U.S. Application Data

[63] Continuation of application No. PCT/US96/16531, Oct. 16, 1996.
[60] Provisional application No. 60/005,359, Oct. 16, 1995.
[51] Int. Cl.$^7$ .......................... C12P 21/06; C12N 15/64; C12N 15/00; A61K 39/12; A61K 39/21
[52] U.S. Cl. ................... 435/69.1; 424/199.1; 424/208.1; 435/69.3; 435/91.42; 435/172.3
[58] Field of Search ................... 435/69.1, 69.3, 435/91.42, 172.3; 424/199.1, 208.1

[56] References Cited

FOREIGN PATENT DOCUMENTS

WO 93/03143  2/1993  WIPO.
WO 95/22618  8/1995  WIPO.

OTHER PUBLICATIONS

Aran J.M. et al., "Drug–Selected Coexpression of Human Glucocerebrosidase and P-glycoprotein using a Bicistronic Vector," *Proc. Natl. Acad. Sci.* USA 91:3176–3180 (1994).

Morgan R. A. et al., "Retroviral Vectors Containing Putative Internal Ribosome Entry Sites: Development of a Polycistronic Gene Transfer System and Applications to Human Gene Therapy," *Nucl. Acids Res.* 20(6):1293–1299 (1992).

Levin R. et al., "Inhibition of Early and Late Events of the HIV–1 Replication Cycle by the Cytoplasmic Fab Intrabodies Against the Matrix Protein, p17," *Molec. Med.* 3(2):96–110 (1997).

Chen B.–F. et al., "Characterization of a Bicistronic Retroviral Vector Composed of the Swine Vesicular Disease Virus Internal Ribosome Entry Site," *J. Virol* 67(4):2142–2148 (1993).

Koo H.–M. et al., "A Spleen Necrosis Virus–Based Retroviral Vector which Expresses Two Genes from a Dicistronic MrNA," *Virol.* 186:675 (1992).

Adam M. A. et al., "Internal Initiation of Translation in Retroviral Vectors carrying Picornavirus 5' Nontranslated Regions," *J. Virol.* 65:4985–4990 (1991).

T. Akagi et al., Gene, vol. 106, 1991, pp. 255–259.

M.L. Lever et al., J. Biochem., Abstract, 1993, p. 250.

M.A. Biasolo et al., Prog. Biotechnol., vol. 9, pp. 685–688.

L. Zitvogel et al., Human Gene Therapy, vol. 5, 1994, pp. 1493–1506. (w/abstract).

M. Gossen et al., Proc.Natl.Acad.Sci. USA, vol. 89, 1992, pp. 5547–5551. (w/abstract).

I.R. Ghattas et al., Mol.Cell.Biol., vol. 11, 1991, pp. 5848–5859.

D.G. Macejak et al., Nature, vol.353, 1991, pp. 90–94.

S.K. Oh et al., Genes & Development, vol. 6, 1992, pp. 1643–1653.

J. Pelletier et al., Nature, vol. 334, 1998, pp. 320–325.

P.S. Mountford et al., TIG, vol. 11, 1995, pp. 179–184.

Y. Sugimoto et al., Human Gene Therapy, vol. 6, 1995, pp. 905–915. (w/ abstract).

*Primary Examiner*—Hankyel Park
*Attorney, Agent, or Firm*—Nixon & Peabody LLP

[57] ABSTRACT

The present invention is related to vectors and methods for increasing the expression of a desired gene product. Preferably this invention is used with genes expressing proteins that are not well tolerated by mammalian cells or where high levels of expression are necessary. In certain preferred embodiments it can be used as part of a multi-tiered expression system and with methods of intracellularly targeting a molecule.

9 Claims, 12 Drawing Sheets negative control sFvTacKDEL single cell subclones sFvTacKDEL single cell subclones sFvTacKDEL single cell subclones anti-Tax immunoblot

EXPRESSION VECTORS AND METHODS OF USE

This application is a continuation of application International Application PCT/US96/16531 filed on Oct. 16, 1996 and which designated the U.S., which claims benefit to U.S. Provisional application 60/005359 filed Oct. 16, 1995.

The present invention is related to vectors and methods for increasing the expression of a desired gene product. Preferably this invention is used with genes expressing proteins that are not well tolerated by mammalian cells or where high levels of expression are necessary. In certain preferred embodiments it can be used as part of a multi-tiered expression system and with methods of intracellularly targeting a molecule.

Problems that have been encountered with the expression of recombinant proteins can include lower levels of expression than necessary for a particular goal and selection against cells expressing such protein. For example, the HTLV-1 and HTLV-2 tax genes are not well tolerated by mammalian cells. Similarly, the hybrid transactivator (tTA protein) of Bujard [Grossen, M., et al., *Proc. Natl. Acad. Sci. USA* 89: 5547–5551 (1992)], which is composed of the DNA-binding domain of the tetracycline repressor fused to the activation domain of the eukaryotic transcription factor VP16, is also not well tolerated by mammalian cells. Thus, in certain instances, cells expressing such proteins will not replicate as fast or as efficiently as cells that do not express such a protein. Accordingly, when one looks for cells expressing such proteins, one sometimes encounters the phenomenon of "silencing" where cells expressing the desired protein are phenotypically not seen.

One classic strategy that has been adopted to deal with that phenomenon is the use of a selectable marker in association with the gene of interest. Thus, by using selection pressure for the selectable marker, one selects only those cells expressing that selectable marker and increase the probability of such cells also expressing the desired gene. However, while this strategy increases the probability that one will obtain a cell that expresses the desired gene, it does not insure such a selection. For example, one typically uses a divalent vector or co-transfection. With co-transfection lower expression can be seen. And, with genes encoding proteins that are not well tolerated by a cell, natural selection can act to favor those cells co-expressing not both the selectable marker and the gene of interest. Consequently, where there is some selection pressure against the desired gene product, that strategy is not entirely effective.

Other strategies to combat such problems have been to use strong promoters and enhancers to increase the expression of desired genes. However, the effectiveness of this approach varies depending upon the particular gene products and cells.

Accordingly, it would be desirable to have vectors and/or methods that would reduce the ability of selection pressure to silence, or otherwise select against such genes.

In addition, there are instances where a very high level of expression is desired to accomplish a desired purpose. For example, with certain cells, where a receptor is a target molecule (e.g. IL-2Rα) although intracellular antibodies can target many of the receptors, some receptors escape and will still appear on the surface. Thus, these receptors can still have an adverse effect. Accordingly, increasing the number of for example intracellular antibodies expressed can enhance the effectiveness of their use.

SUMMARY OF THE INVENTION

We have now discovered novel vector systems and methods which can be used for increasing expression of a desired gene.

In one embodiment this invention relates to the use of internal ribosome entry site (IRES) to link a selectable marker with a gene of interest. This permits "forced-expression" of the desired gene. Still more preferably the vector would contain a strong promoter that will result in high levels of expression and/or enhancers or other genes or genetic factors that increase gene expression. For example, the inclusion of an HIV tar element. When a tat is added to a gene operatively linked to a TAR element, it results in transactivation and the resultant expression of extremely high levels of that gene. The tat gene may or may not be present as part of the vector.

In an alternative embodiment one uses a vector such as a lentivirus vector, for example an HIV vector, having multiple splice acceptors and splice donors, thereby resulting in the inclusion of additional introns. The presence of introns in that type of vector system result in enhanced levels of expression. More preferably, this vector can be used with IRES sequences.

BRIEF DESCRIPTION OF THE DRAWINGS

FIGS. 5A through 5J show the FACS analysis of IL-2Rα expression on Jurkat and C8166 transfected cells with a forced expression vector of the present invention expressing sFvTacKDEL.

FIG. 9A is a growth curve, FIG. 9B is a western block, FIG. 9C shows thymidine incorporation.

DETAILED DESCRIPTION OF THE PRESENT INVENTION

Figure 1:
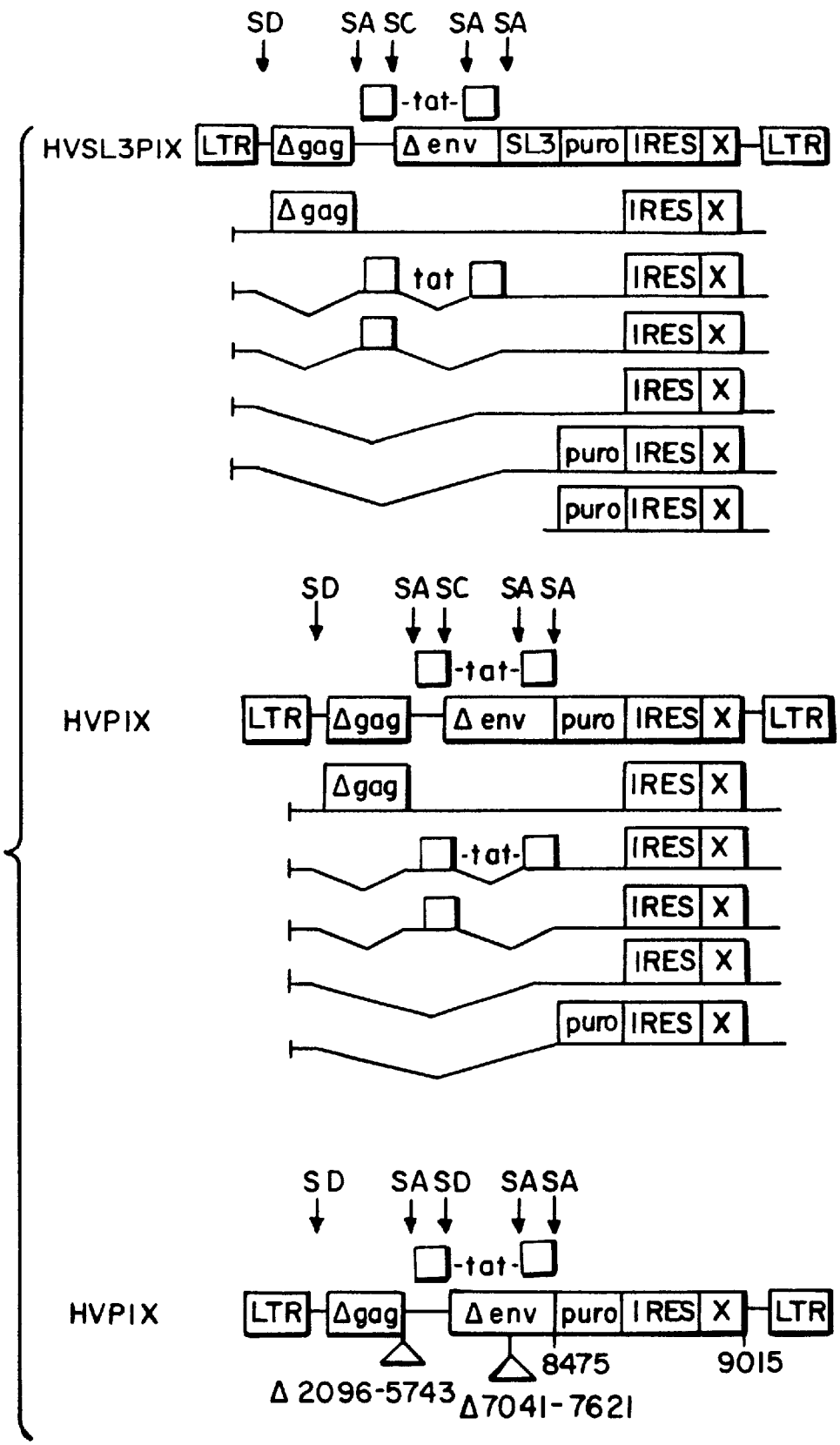
FIG. 1 is a schematic showing the structure of HIV-1 based retroviral vectors that can be used in the present invention. Deletions in genes are indicated by sequence numbers. Splice acceptor (SA) and splice donor (SD) sites are also indicated. X indicates a gene of interest. The major RNA species are also shown.

We have discovered that using IRES sequences in a vector results in a stronger linkage between different genes than is seen with using multiple promoters in a multivalent vector. Consequently, by appropriate selection of one of the genes, one can obtain "forced expression" of a desired gene. This permits selection of such a gene where it normally would be selected against.

For example, the HTLV 1 and HTLV 2 tax genes are typically not well tolerated by normal cells. Thus, even where a multivalent vector is used for tax expression and one uses a marker gene such as puromycin resistance marker (puro) to select transformed cells minimal or no detectable tax expression is seen in stably transduced peripheral blood T lymphocytes by Western blot analysis. This is because there is a selection against those cells also expressing the tax gene. Thus, transformed neo or puro cells not expressing tax are being selected. As a further example, we have found that there may also be a selection in certain cell lines against certain of the antibodies expressed intracellularly (intrabody) for tac and that one can also see silencing. This is a phenomenon that can occur with a wide range of different gene products as well including tTA, genes for other intrabodies, etc, depending upon the particular cell line used. Whether a gene product is or is not well tolerated by a particular cell line can readily be determined empirically by known techniques. For example, one can do simple in vitro tissue culture tests and compare expression of the desired product with its production in a naturally expressing cell line, or with a similarly sized gene product.

Selectable markers are well known in the art and include genes that express proteins that change the sensitivity of a cell to a stimuli such as a nutrient, an antibiotic, etc. Genes include those for neo, puro, tk, multiple drug resistance (MDR), etc.

We have now discovered that using vectors containing IRES can result in multicistronic RNA that can link a gene of interest such as an sFvTac with a selectable marker more effectively than seen in multivalent vectors. The resultant products of that IRES linkage are not fusion proteins, and they exhibit their normal biological function. Accordingly, the use of these vectors permits the forced expression of a desired protein.

IRES sequences act on improving translation efficiency of RNAs in contrast to a promoter's effect on transcription of DNAs. A number of different IRES sequences are known including those from encephalomyocarditis virus (EMCV) [Ghattas, I. R., et al., *Mol. Cell. Biol.*, 11:5848–5859 (1991); BiP protein [Macejak and Sarnow, *Nature* 353:91 (1991)]; the Antennapedia gene of *drosphilia* (exons d and e) [Oh, et al., *Genes & Development*, 6:1643–1653 (1992)]; as well as those in polio virus [Pelletier and Sonenberg, *Nature* 334: 320–325 (1988); see also Mountford and Smith, TIG 11, 179–184 (1985)].

IRES sequences are typically found in the 5' noncoding region of genes. In addition to those in the literature they can be found empirically by looking for genetic sequences that effect expression and then determining whether that sequence effects the DNA (i.e. acts as a promoter or enhancer) or only the RNA (acts as an IRES sequence).

One can use these IRES sequences in a wide range of vectors ranging from artificial constructs (such as in U.S. Ser. No. 08/199,070, filed Feb. 22, 1994 to Marasco, et al.; PCT No. PCT/US95/02140) to DNA and RNA vectors. DNA vectors include herpes virus vectors, pox virus vectors, etc. RNA vectors are preferred. Still more preferably one uses a retroviral vector such as a lentivirus vector such as HIV, SIV, etc. These vectors are sometimes referred to as defective vectors, and as used herein that term means that while the vectors retain the ability to infect, they have been altered so they will not result in establishment of a productive wild-type disease.

We found that lentivirus vectors typically contain multiple splice acceptors and splice donor sites (See FIG. 1). The presence of these splice donor and acceptors can result in enhanced levels of expression of the desired protein. FIG. 1 shows the potential transcription/translation products produced. Six RNA species for HVSL3PIX are shown and five species for HVSL3PIX. In these species whether or not a particular gene is expressed depends upon the splice acceptor and splice donor sites and then the gene's position upon reentry. In these constructs, we believe most of the transcripts have the gene of interest (X) and this also accounts for its high level of expression. Thus, although not wishing to be bound by theory, we believe enhanced levels of expression are obtained because these vectors contain introns.

The vectors containing multiple splice acceptors and donor sites can be used in an alternative embodiment without an IRES sequence.

In addition to using these vectors with genes that are not well tolerated by a particular cell, there are instances where extremely high levels of a particular gene are desired. For example, when targeting a receptor where even the presence of a small number of receptors can permit an undesired result, e.g. infection by a virus such as with CD4 and HIV, malignant transformation of a cell, inappropriate signal transduction.

For example, we have found that the intracellular expression of an antibody such as one for Tac (e.g. sFvTacKDEL) can be expressed in certain cells (e.g. Jurkat) but not be entirely effective in other cells (e.g. C8166), where some IL-2R$\alpha$ receptors are seen. However, we have been able to obtain high levels of an intrabody with a vector of the present invention. For example, a forced expression HIV-1 vector containing IRES sequences and multiple splice acceptance and splice donor sites (See FIG. 1 and FIGS. 4–8).

This vector uses the 5' HIV LTR which contains a promoter and also the TAR element. In that vector the genes of interest are operably linked to the TAR element. Thus, when tat interacts with the TAR element, the gene is trans-activated resulting in high levels of expression. In one embodiment one can supply tat by including the tat gene as part of the vector. See FIG. 1. One can also include a rev responsive element (RRE) to further tailor expression. When an RRE is used, rev is necessary for efficient expression of the gene the RRE is linked to (See the first transcript in FIG. 1). The gag RRE is present, thus this species is rev dependent. In other embodiments one can use the TAR element as part of an inducible or multi-tiered system. Thus, for example, if one wishes to use for example an intrabody that one wishes to have expressed at high levels only at certain times, for example (a gene for an intrabody for the HIV envelope gene or the HIV gag gene) in the presence of HIV virus one would not include the tat gene as part of such a vector. Similarly, there are other instances where one would specifically want to either co-transfect the cell with the tat gene at a specified time or supply tat proteins as a specified time. In those instances one would also not include the tat gene as part of the vector.

In such instances, one might also want to use a different promoter than the promoter region in the HIV LTR. Promoters are well known in the art and can readily be selected depending upon the particular cell line that one wishes to have expression. Promoters that will permit expression in mammalian cells are well known and include cytomegalovirus (CMV) intermediate early promoter, viral LTRs, such as the rous scaroma virus, the HTLV-1 LTR, the simian virus 40 (SV 40) early promoter, E. coli lac UV 5 promoter and the herpes simplex tk virus promoters.

Figure 10:
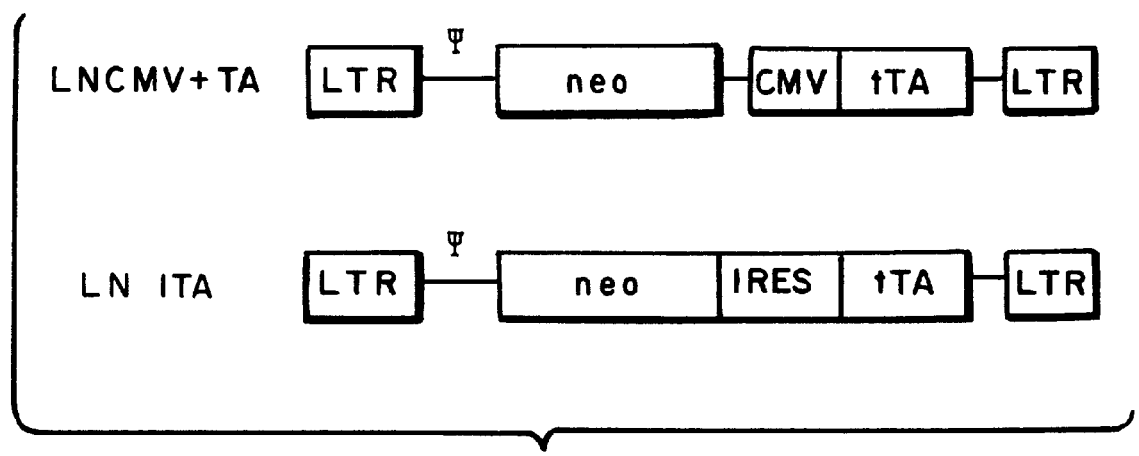
FIG. 10 is a schematic showing the structure of MLV retroviral vectors used to compare forced and unforced expression.

For example, we have found that using a known MMLV retroviral, vector, e.g. the LN vector of D. Miller, we have been able to obtain forced expression with a poorly expressed gene in C8166 cell lines. See FIG. 10. The tTA protein is selected against and poorly expressed under normal conditions. Thus, for example, with the vector LNC-MVtTA (a divalent vector wherein the neo gene is under the control of the MMLV LTR promoter and the tTA is under the control of an interval CMV promoter) we found that the percent of G418 resistance cells that also express tTA was zero (0/12). In contrast, when we linked expression of tTA to the expression of the neo by using a IRES sequence, in an identical vector, substituting the EMCV IRES sequence for the CMV promoter we obtained expression of tTA 80% of the time in those cells that demonstrated G418 resistance (8/10).

Figure 9A:
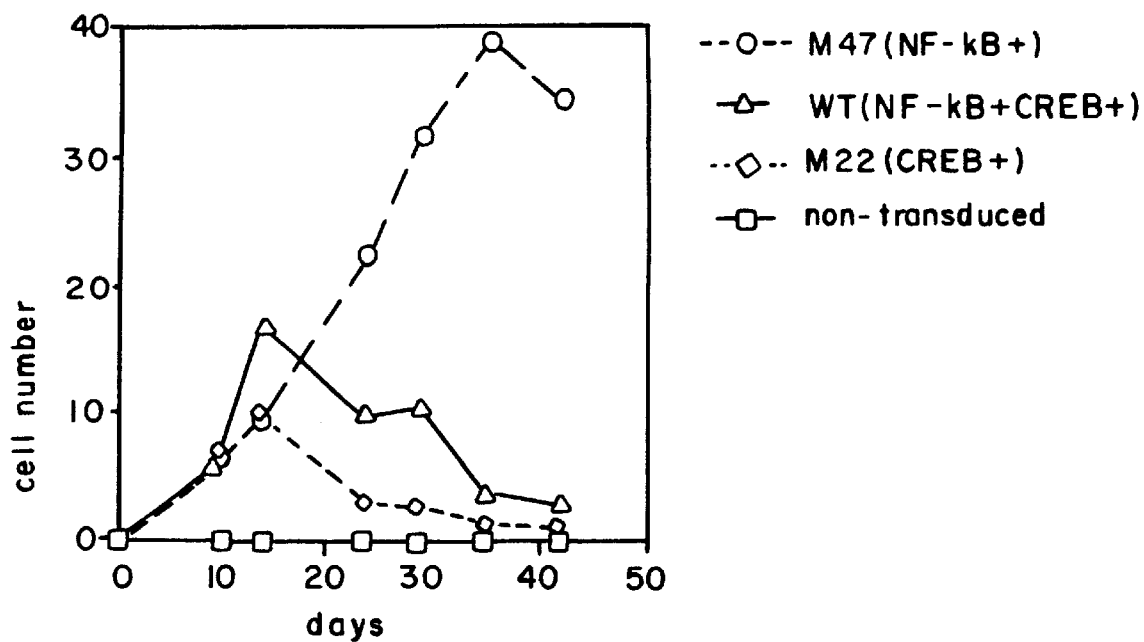
FIGS. 9A through 9C show that tax expression using vectors of the present invention is at least as great with the present invention as is seen in a natural tax high expressor cell line, C8166. WT stands for wild-type tax. M47 and M22 are two tax mutants.
Figure 9B:
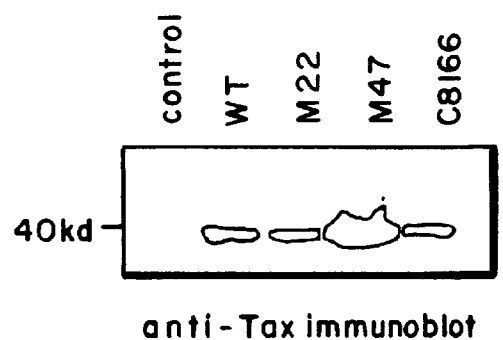
Figure 9C:
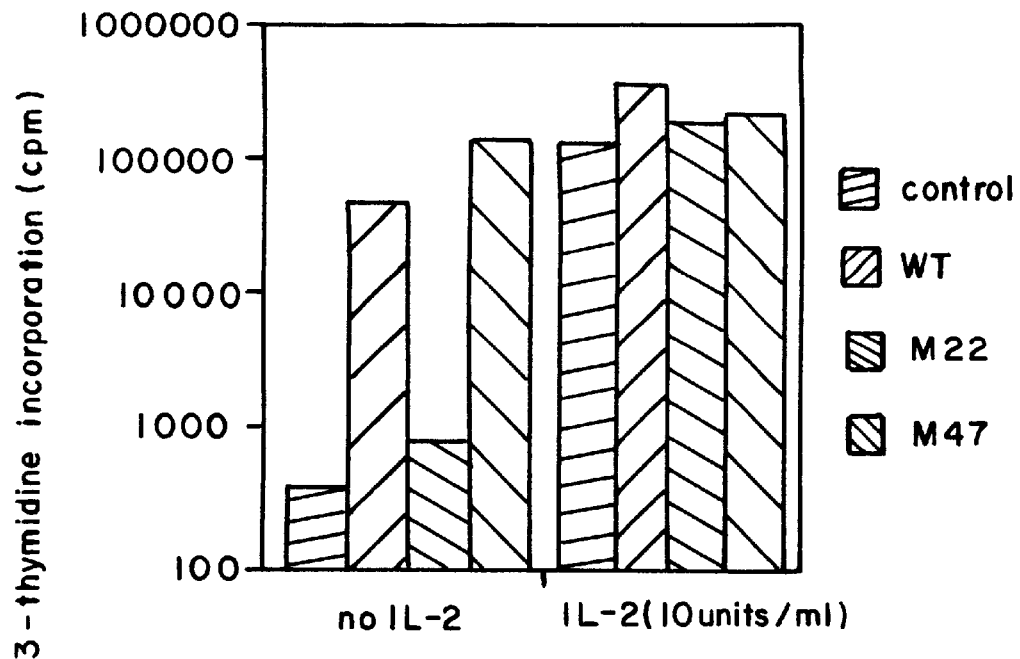

The tax gene is typically selected against. Thus, divalent MMLV vectors where tax was under the control of an LTR and a selectable marker either puro or neo were under the control of the SV40 promoter gave minimal or no detectable expression in stably transduced PBMCs as determined by western blot analysis, i.e. there was undetectable expression and no phenotypic response. In contrast, when we used an IRES sequence to result in forced expression using the puro gene in an HIV forced expression vector we obtained easily measurable tax protein levels as determined both by Western blot analysis and biological phenotype (See FIGS. 9A–9C). Indeed as shown in FIG. 9B, the level of expression of tax (WT) as well as a variety of different tax mutants (M22 and M47) was as high or higher than the tax expression seen in an HTLV-1 transformed cell line that is a high expresser of tax, C8166.

We have also demonstrated that our forced expression system works with genes for intrabodies. See, FIGS. 4–8.

The forced expression vectors can be used in a variety of different systems ranging from in vitro to in vivo. For example, one difficulty encountered with ex vivo somatic cell therapy is the relatively poor rate of transfection frequently seen when retroviral are used. vectors. This requires difficult selection methods and, as shown herein, even when selecting using a marker gene, if the other gene is not well-tolerated by this cell, one often will not be obtaining a transformed cell that will also express the gene of interest. Thus, the present system is particularly useful with such cells, for example, with transforming bone marrow cells.

The present system can also be used to enhance in vivo selection. In this instance, one must choose the appropriate marker. Such markers are well known and include those that would make certain cells more (e.g. using the tk gene) or less susceptible (e.g. using the MDR gene) to certain other agents. For example, one can use the method of intracellular targeting of cells in conjunction with other therapies. Frequently after initial exposure to certain treatments a tolerance is rapidly developed making those treatments relatively ineffective or totally ineffective. Thus, one method of using forced expression is to include a gene that provides resistance against that therapy. For example, transforming non-tumor cells surrounding a tumor with an intrabody linked to a taxol resistant gene or an MDR gene prior to chemotherapeutic treatment. The treatment would kill the majority of non-transduced cells, and select for transduced cells expressing the intrabody.

The expression vectors can be used to transform cells by any of a wide range of techniques well known in the art, including electrophoresis, calcium phosphate precipitation, catheters, liposomes, etc.

The amount of vector one would use would depend upon the particular use. For example, one could inject sufficient amount of the vectors to obtain a serum concentration of the desired protein ranging between about 0.05 $\mu$g/ml to 20 $\mu$g/ml of desired protein. More preferably, the range should between about 0.1 $\mu$g/ml to 10 $\mu$g/ml. Still more preferably, between about 0.5 $\mu$g/ml to about 10 $\mu$g/ml.

The vectors, as aforesaid, can be administered by a wide range of techniques including parenteral injection, intraperitoneal, intravenous, intracranial, subcutaneous, oral, or other known routes of administration.

The materials can be administered in any convenient means. For example, it can be mixed with an inert carrier, such as sucrose, lactose, or starch. It can be in the form of liposomes or other encapsulated means. It can also be as part of an aerosol.

Typically, when administered to a host animal, it will be injected in a sterile aqueous or non-aqueous solution, suspension, or emulsion in association with a pharmaceutically acceptable parenteral carrier such as physiological saline.

The present invention is further illustrated by the following examples, which are provided to aid in the understanding of the invention and are not construed as a limitation thereof.

EXAMPLES

Two retroviral cassettes having the structure shown in FIG. 1 were prepared using known techniques. Three deletions in HIV-1 proviral clone HXBC2 (2096–5743), (7041–7621) and (8475–9015) removed part or all of the gag, pol, env, rev, vif and nef open reading frames. The two exons of tat are intact, as are the splice donor and acceptor sites required for tat mRNA expression. By using appropriate endonucleases the tat gene can also be inactivated. A cassette composed of a puromycin acetyl transferase gene (puro), an internal ribosome entry site (IRES or RES) (the EMCV $5^1$ IRES) and a second gene (gene X) were inserted at position 8475, immediately downstream of a naturally occurring splice acceptor site. The resulting vector was designated HVPIX.

In the vector HVSL3PIX, an internal SL3 promoter was incorporated upstream of puro providing an alternative expression mechanism for the puro-IRES-X cassette. This permits tat-independent expression. This can be used in the context of a self inactivating vector. The rev responsive element (RRE) was retained to maximize production of the full length vector RNA in the packaging cell (where rev is supplied in trans).

In the target cell, the absence of rev ensures that only terminally spliced mRNAs (or those initiated at the internal promoter) will be produced. This strategy (i) maximizes expression of mRNAs encoding tat and the 3' heterologous genes (ii) safeguards against the production of full length or partially spliced (env) RNAs which could potentially be packaged by a coinfecting (or endogenous) retrovirus or be translated to produce immunogenic gag or env fragments. We have termed these constructs "forced expression vectors", as the selectable marker gene (puro) and the gene of interest (X) are translated from the same mRNA. This strategy eliminates the possibility of promoter suppression and has allowed the expression of genes which are not tolerated well by mammalian cells such as (tTA) and tax.

Vector encapsidation and transduction

Figure 2:
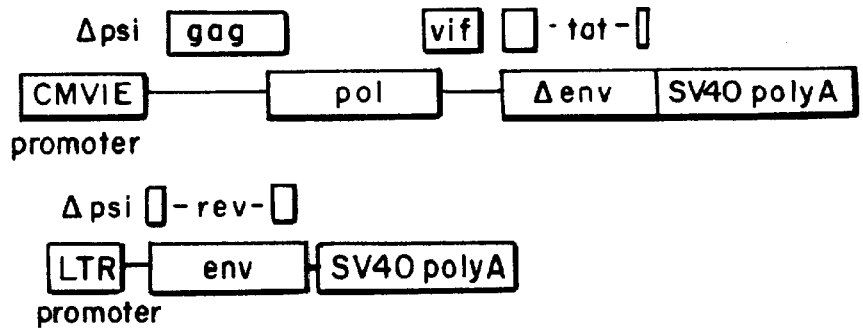
FIG. 2 shows a schematic of helper virus constructs that can be used with the vectors of FIG. 1 to result in HIV vector encapsulation for use in transforming cells.

The vector constructs were introduced into target cells in the form of a conventional retrovirus vector. In the absence of a stable packaging cell line for HIV-1 vectors, vector particles were generated by transiently transfecting COS-1 cells with the vector and two plasmids encoding a HIV-1 helper virus (FIG. 2). Each of the plasmids contained an SV40 origin of replication allowing high level expression in COS-1 cells and the helper virus genome contained multiple cis-acting replication defects which prevent its own transmission.

5–10 μg each of vector and packaging plasmids were cotransfected into COS-1 cells using the DEAE dextran technique. Virus-containing supernatants were harvested 48 and 72 hours later and used immediately to infect target cells. Puromycin selection was applied 24–48 hours after the second infection at 0.5 μg/ml.

Using known techniques, the above strategy can be varied to create stable packaging cell lines.

Vector transfer into primary T-lymphocytes

Ficoll separated peripheral blood mononuclear cells (PBMCs) were stimulated with 1 μg/ml phytohaemagglutinin (PHA) at 1×10$^6$ cells/ml in RPMI-1640 supplemented with 10% fetal bovine serum. Interleukin 2 (IL-2) was added 48 h later (day 2) at 10 units/ml. The following day, 2×10$^6$ cells were infected with 2–5 ml of the vector stock. The infection was repeated with fresh virus on day 4. 48 hours later, puromycin selection was applied at 0.5 μg/ml. Transduced PBMCs were fed at 3–4 day intervals with medium containing IL-7 (100 units/ml) and puromycin. Those cells still viable on day 14 were restimulated with PHA and feeder cells, except that IL-7 was substituted for IL-2 as a T-cell growth factor. Puromycin selection was temporarily withdrawn during the stimulation in order not to poison the feeder cells, but was reapplied after 3 days and maintained thereafter. 7–14 days later, the emergent puromycin resistant cell population was analyzed for cell surface phenotype, intrabody expression, etc.

Generation of single cell subclones

A. Established Cell Lines

Bulk populations of transduced cells were seeded at one cell per well of a 96-well plate with 25% conditioned medium.

B. PBMC Lines

T cell clones were generated by standard techniques. Briefly, 14 days after the previous stimulation, vector-containing (puromycin resistant) cells were seeded at one cell per well of a 96-well plate in the presence of PHA, feeder cells and IL-7. Wells were fed at 3–4 day intervals with medium containing IL-7. Positive wells were restimulated on day 14.

FACS analysis

For detection of cell surface IL-2Rα expression, cells were analyzed by flow cytometry after staining with the anti-tac monoclonal antibody followed by FITC-conjugated goat anti-mouse IgG.

Immunoprecipitation

Metabolic labelling and immunoprecipitations were performed. Briefly, 1×10$^7$ cells were metabolically labelled with $^{35}$S cysteine and then lysed. sFvTac and IL-2Rα were immunoprecipitated using a polyclonal rabbit serum against mouse IgG and the mAb 7G7/B6 respectively.

Measurement of IL-2 induced proliferation

7–10 days after PHA stimulation, cells were washed three times to remove traces of IL-2, then plated in triplicate at 1×10$^5$ cells per well of a 96-well round bottom plate. IL-2 was added at doses ranging from 0 to 100 units/ml. 48 hours later, wells were pulsed with 1 μCi tritiated thymidine. Cells were harvested 18 hours later and thymidine incorporation was measured by liquid scintillation counting.

Results

Insufficiency of other expression vectors

Figure 3:
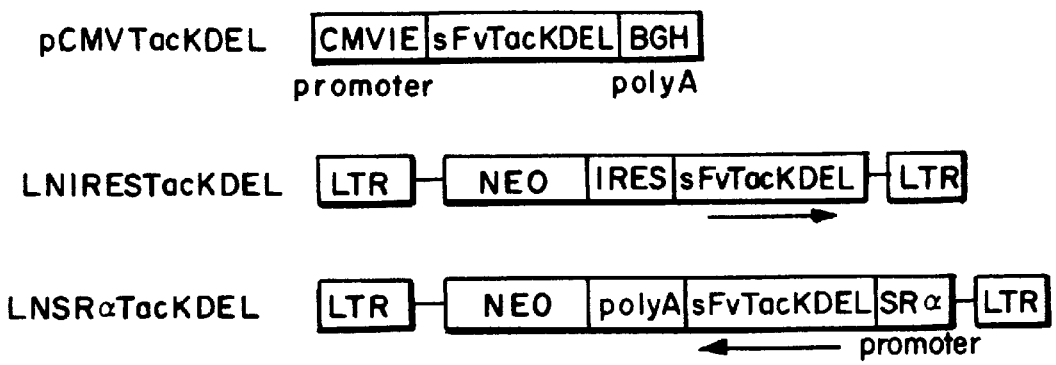
FIG. 3 shows Moloney Murine Leukemia Viral (MMLV) vectors that can be used with the gene of interest in the embodiment shown herein. One gene of interest is for a specific single chain antibody for Tac referred to as sFvTacKDEL.

We had previously attempted to express the sFvTacKDEL intrabody in HTLV-1 transformed cell lines using the vectors illustrated in FIG. 3. Those vectors are produced from MMLV vectors using standard means, e.g. the sFvTac gene was reamplified by PCR, digested with appropriate endonucleous, and ligated into the vector. Although the intrabody expression levels obtained with pCMVTacKDEL were sufficient to downregulate IL-2Rα in Jurkat cells, which express ~9,000 molecules per cell, the vectors shown in FIG. 3 had little or no impact on cell surface expression of IL-2Rα in HTLV-1 transformed cell lines which express much higher levels of the receptor (~200,000 molecules per cell) (FIG. 4). Immunoprecipitation analysis revealed only trace amounts of the sFvTacKDEL intrabody in the stably transfected cells (not shown).

Possible reasons for the inability of these vectors to inhibit IL-2Rα expression include:

counter selection of cells which have downregulated the receptor, owing to a biological requirement for IL-2Rα expression in these cells counter selection of cells which have downregulated the receptor, owing to a toxic accumulation of immune complexes in the ER or golgi inadequate expression levels of the sFvTacKDEL intrabody for the goal desired On the basis of data presented below, although not wishing to be bound by theory we have excluded the first two possibilities, suggesting that efficiency of intrabody gene expression was important in determining the successful outcome of this approach with these cells.

FIG. 3 shows diagrams of the vectors pCMVTacKDE1, LN-IRES-TacKDEL, LN-SRαTacKDEL.

FIG. 4 shows FACS analysis of C8166 cells transfected with above vectors and showing normal levels of IL-2Rα.

Highly efficient downregulation of IL-2Rα in HTLV-1 transformed cell lines using the HIV-1 forced expression vector.

Jurkat and C8166 cells were transduced with the vectors HVSL3PITacKDEL or HVPITacKDEL as described above. Bulk populations of puromycin-selected cells were analyzed for cell surface IL-2Rα expression by flow cytometry. Jurkat cells were stimulated for 18 hours with PHA and PMA prior to immunostaining. As shown in FIG. 5, a vast majority (>95%) of the puromycin resistant cells were completely negative for IL-2Rα expression when stained with the anti-tac mAb. The same result was obtained when the cells were stained with the mAb 7G7/B6, which recognizes a different epitope. This indicates that the lack of staining with anti-tac is not due to masking of the tac epitope by secreted sFvTacKDEL.

Immunoprecipitation of IL-2Rα from the transfected C8166 cells revealed:

a complete absence of mature (55 kDa) receptor chains intracellular accumulation of the 40 kDα IL-2Ra precursor coprecipitation of sFvTacKDE1 with the 40 kDa precursor Together, these findings suggest that the absence of mature p55 at the cell surface is due to retention of the immature p40 form in the ER, as a complex with sFvTacKDE1.

These results have been reproduced in two other T leukemic cell lines which express high levels of IL-2Rα. HUT102, an HTLV-1 transformed line, and the Kit225 line. The Kit225 cells are growth factor dependent and were maintained on 100 units/ml IL-7. After introduction of the HIV-1 forced expression vector into these cell lines, a majority of the bulk transduced population were negative for IL-2Rα expression. By subcloning from the bulk population, homogenous negative clones were obtained (FIG. 6).

Efficient downregulation of IL-2Rα and reduced IL-2 responsiveness in PBMCs transduced with the sFvTacKDEL forced expression vector.

Figure 8:
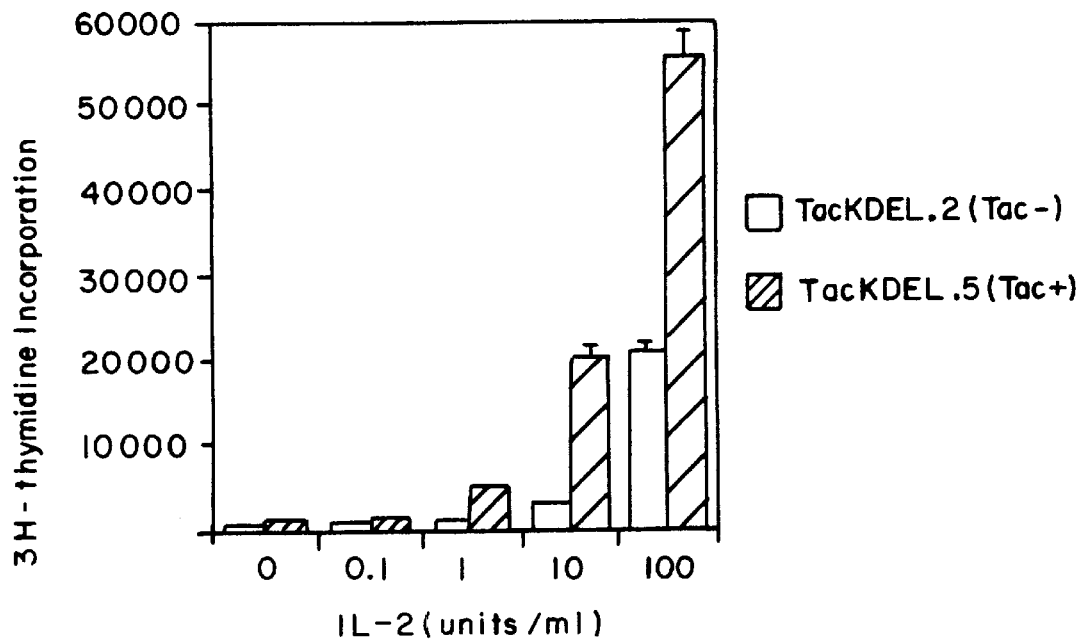
FIG. 8 is a graph showing the diminished IL-2 responsiveness of IL-2Rα negative T cells.
Figure 4A:
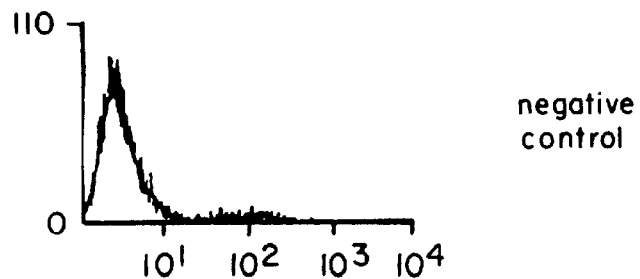
FIGS. 4A through 4G show the FACS analysis of cell surface expression of IL-2Rα on C8166 cells.
Figure 4B:
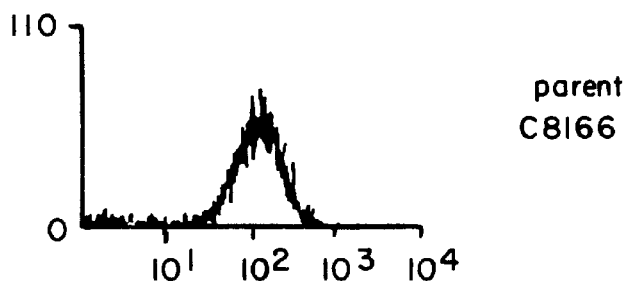
Figure 4C:
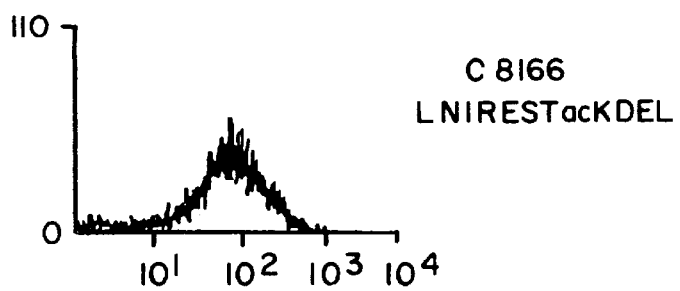
Figure 4D:
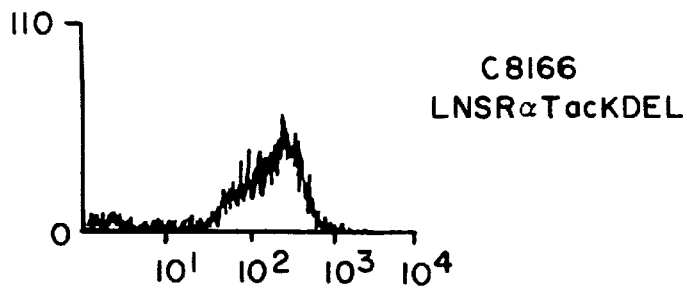
Figure 4E:
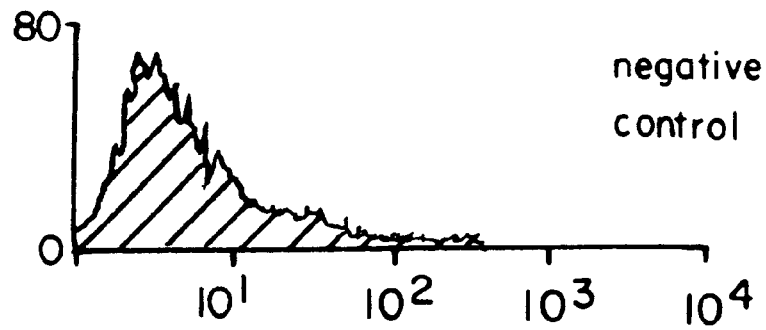
Figure 4F:
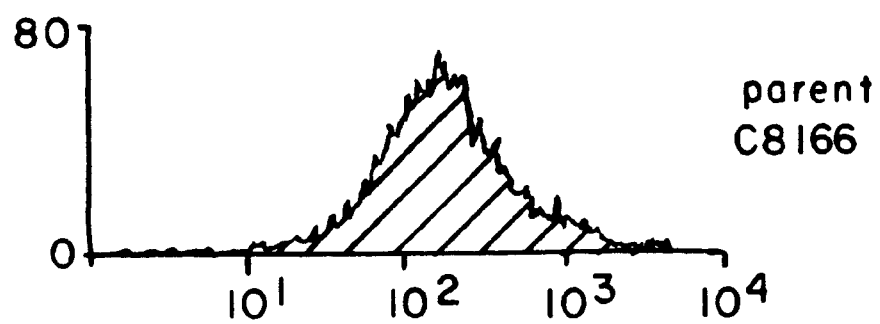
Figure 4G:
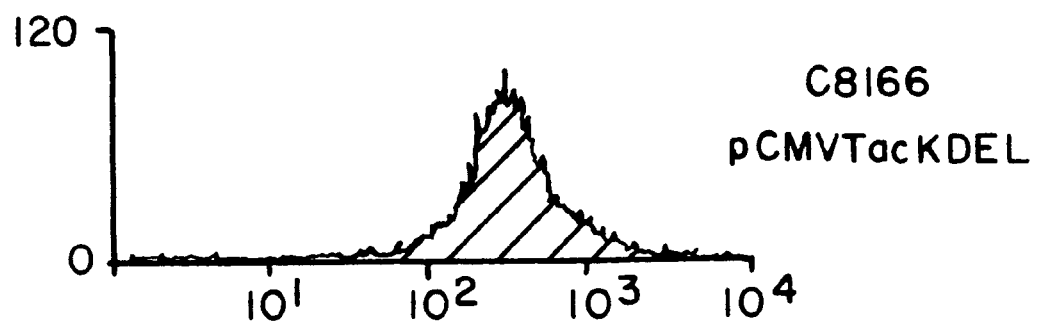
Figure 5A:
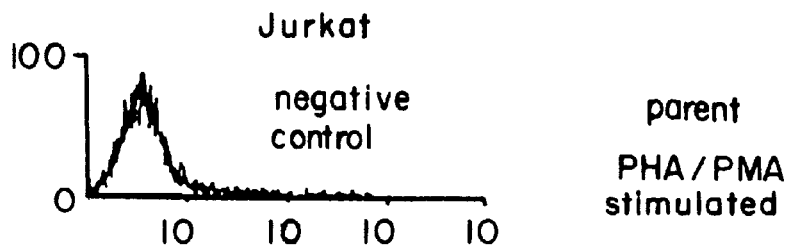
Figure 5A:
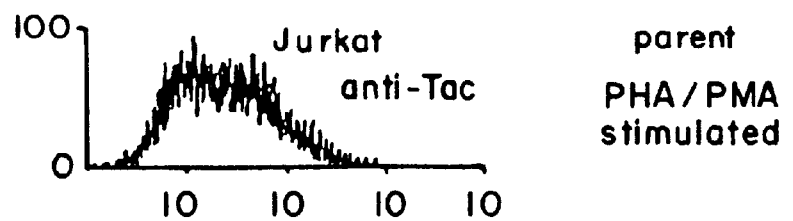
Figure 5C:
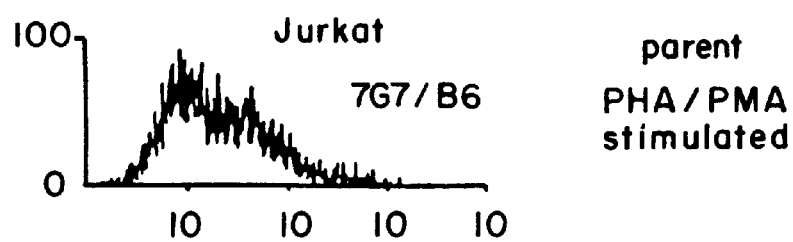
Figure 5D:
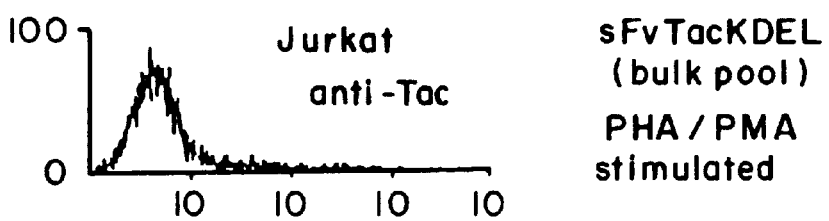
Figure 5E:
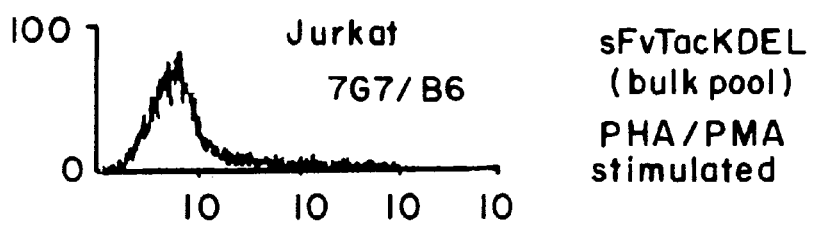
Figure 5F:
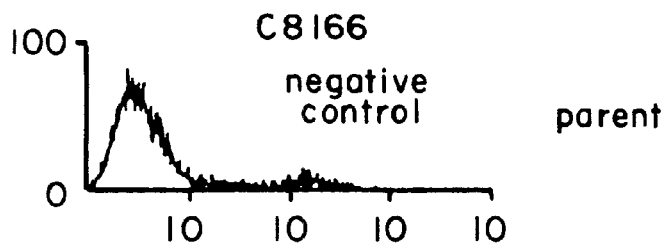
Figure 5G:
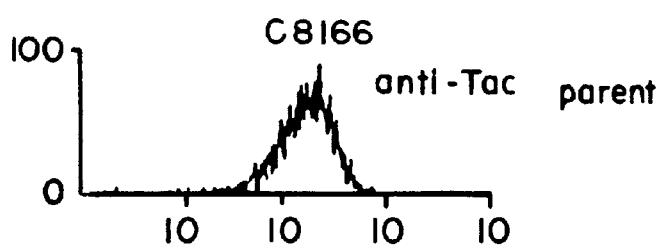
Figure 5H:
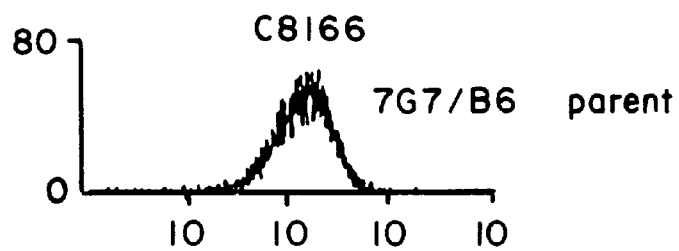
Figure 5I:
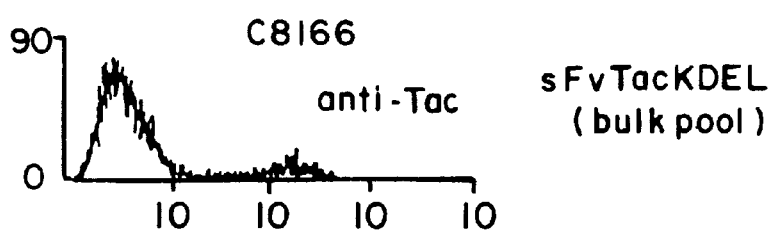
Figure 5J:
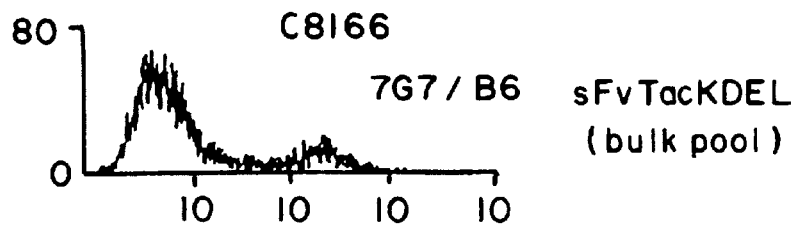
Figure 6A:
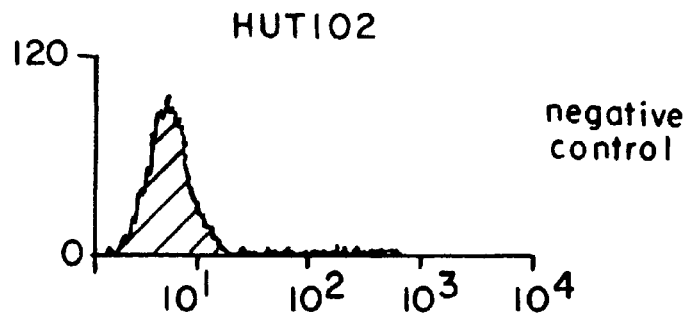
FIGS. 6A through 6H show the FACS analysis of IL-2Rα expression on HUT102 and Kit225 cells transfected with a forced expression vector of the present invention, the sFvTacKDEL forced expression vector.
Figure 6B:
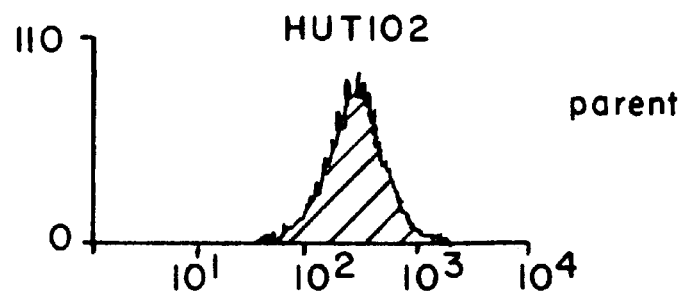
Figure 6C:
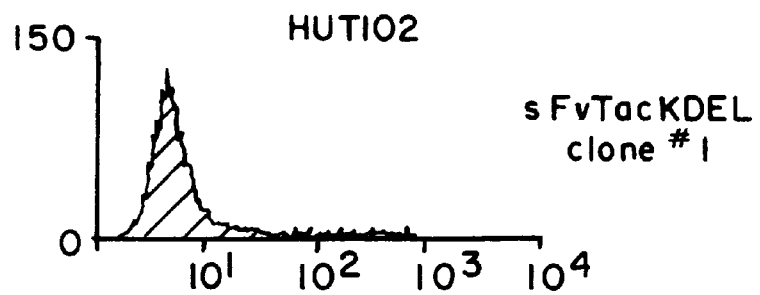
Figure 6D:
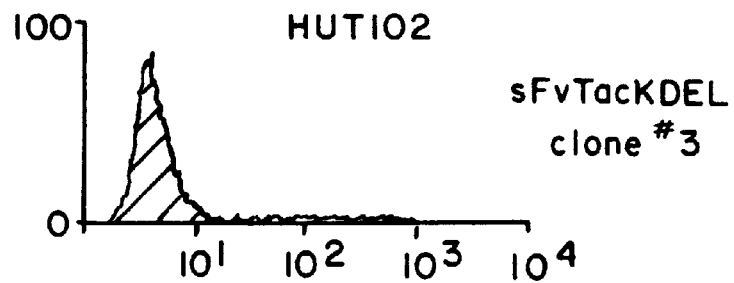
Figure 6E:
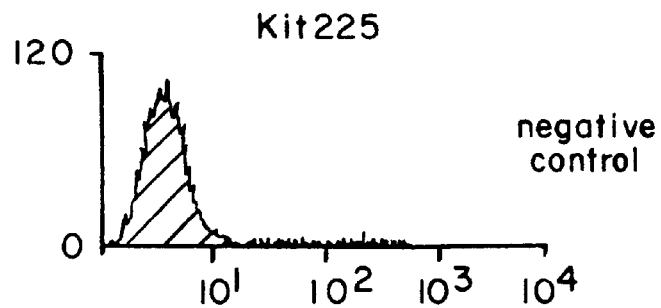
Figure 6F:
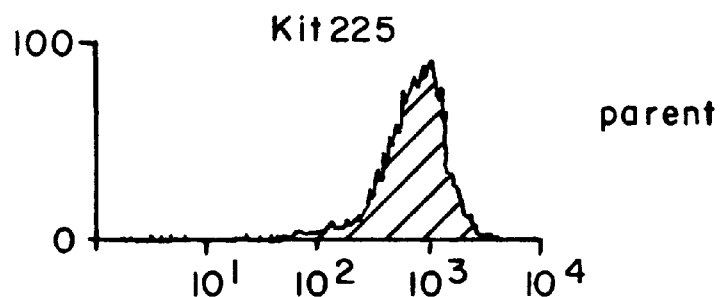
Figure 6G:
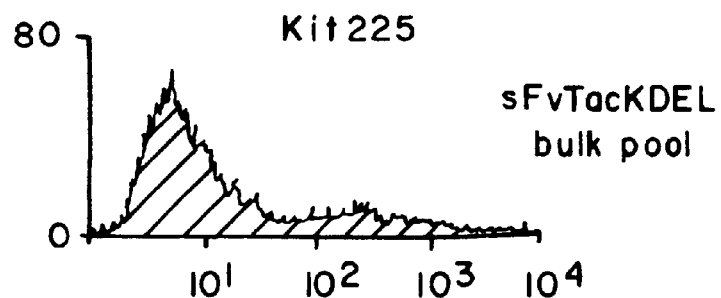
Figure 6H:
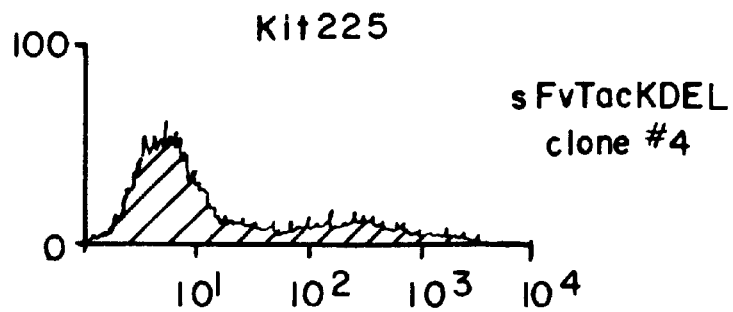
Figure 7A:
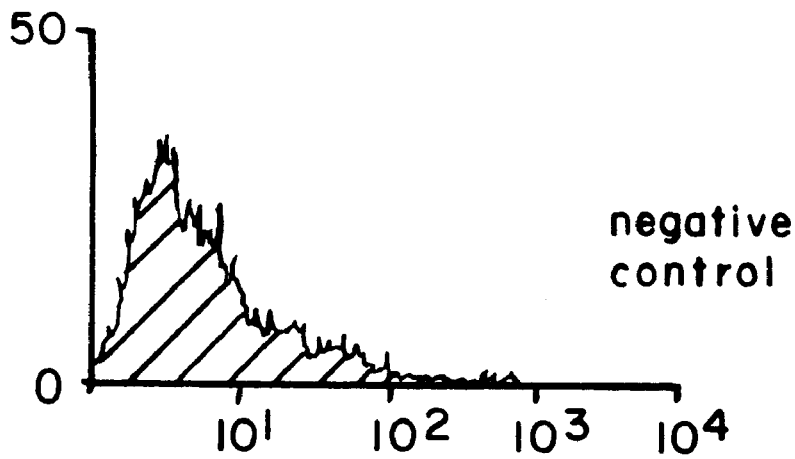
FIGS. 7A through 7G show the FACS analysis of IL-2Rα expression on peripheral blood T lymphocytes transfected with the sFvTacKDEL forced expression vector.
Figure 7B:
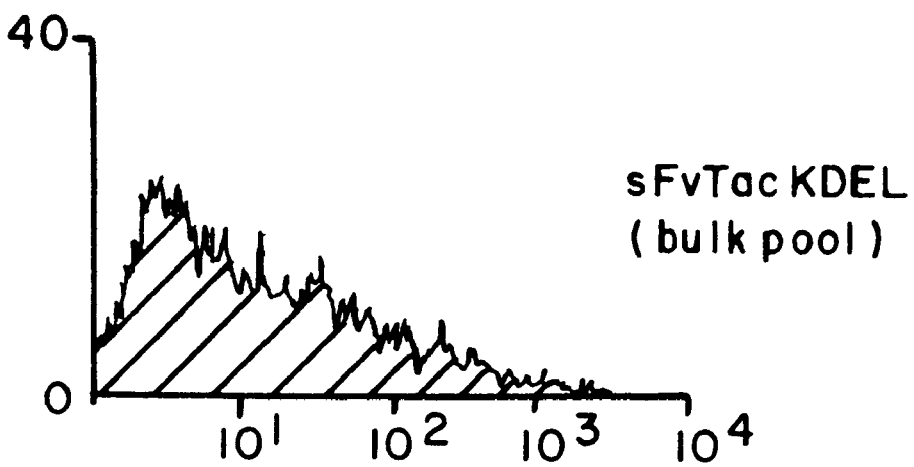
Figure 7C:
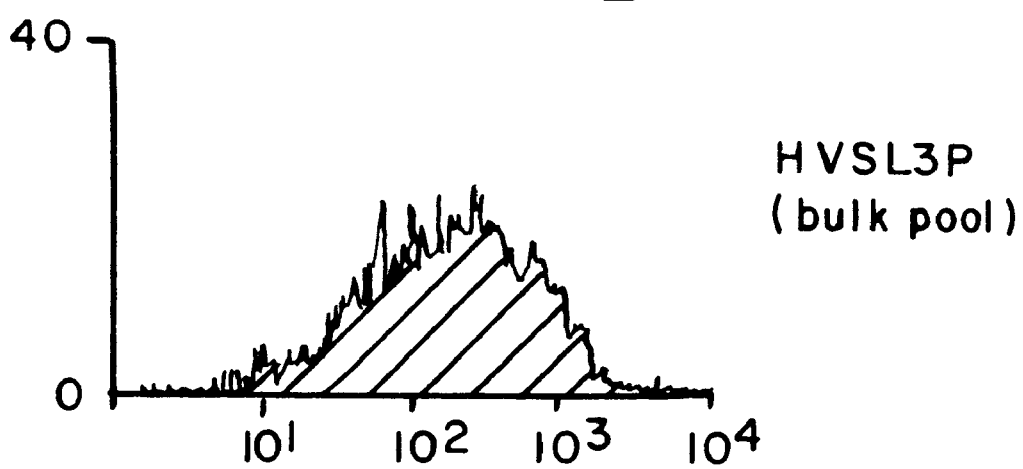
Figure 7D:
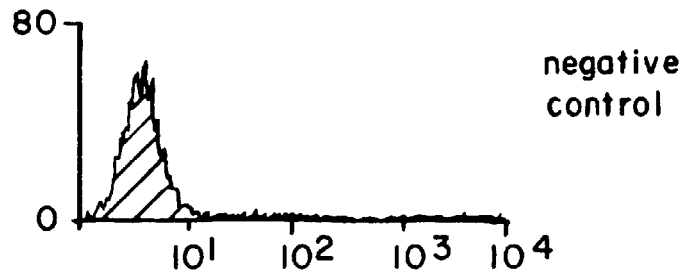
Figure 7E:
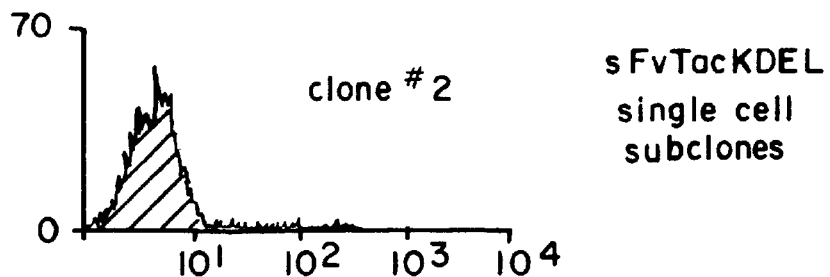
Figure 7F:
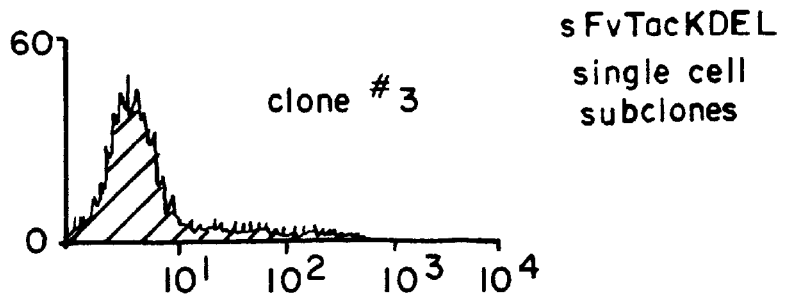
Figure 7G:
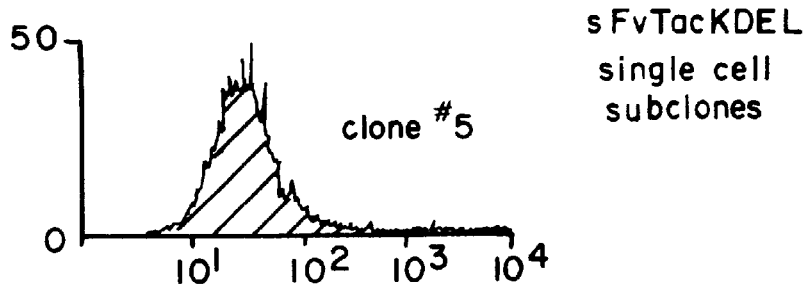

FIG. 7 shows IL-2Rα expression on PHA-activated peripheral blood mononuclear cells transfected with the sFvTacKDEL forced expression vector or a control vector (1) bulk population (FIGS. 7A–C); or (2) single cell subclones (FIGS. 7D–G). Flow cytometric analysis of a bulk PBMC population transduced with the HIV-1 forced expression vector showed virtually no IL-2Rα expression (FIG. 7B) in comparison to a control population transduced with an irrelevant (empty) vector HVSL3P (FIG. 7C). These cells were generated and maintained in the presence of IL-7, an alternative T cell growth factor. By subcloning (FIG. 7B), single cell clones were obtained that express no detectable IL-2Rα (See FIGS. 7E and F). A thymidine incorporation assay was used to measure the IL-2 responsiveness of the IL-2Rα negative clones (FIG. 8). FIG. 8 shows IL-2 induced proliferation in peripheral blood T cell clones which are positive (clone 5) or negative (clone 2) for IL-2Rα expression. These clones did not respond to low doses of IL-2 (1 unit/ml). Some proliferation was seen at doses of 10 and 100 units/ml but when compared to an IL-2Rα-positive clone, −10 times more IL-2 was required to achieve an equivalent proliferative response. Some IL-2 responsiveness was expected, even in the absence of IL-2Rα, as these cells will still express intermediate affinity receptors for IL-2. These data demonstrate functional as well as phenotypic evidence for the absence of high affinity IL-2 receptors in the IL-2Rα negative cells.

We claim:

1. A lentiviral vector containing a gene of interest operably linked to a selectable marker gene by an internal ribosome entry site (IRES).

2. The lentiviral vector of claim 1, wherein the gene of interest is a gene whose expression in a mammalian cell is selected against as determined by comparing a cell transduced using a divalent vector or co-transfection with a selectable marker and said gene, with a control cell transduced using a divalent vector or co-transfection with only said selectable marker.

3. The lentiviral vector of claim 2, wherein the gene of interest is selected from the group consisting of a gene for HTLV-1 tax, HTLV-2 tax, an antibody and a protein that is part of a multi-tiered expression system.

4. The lentiviral vector of claim 1, wherein a defective lentiviral vector is used.

5. The lentiviral vector of claim 4, wherein the defective lentiviral vector is a lentiviral vector containing multiple splice donor and splice acceptor sites.

6. The lentiviral vector of claim 5, wherein the lentiviral vector is an HIV viral vector.

7. A method of using the vector of claim 1 to obtain forced expression of the gene of interest which comprises using the vector of claim 1 to transduce a mammalian cell, culturing the transduced cell under conditions sufficed to express the selectable marker gene, and then exerting selection pressure on the transduced cell to select for that selectable marker.

8. The lentiviral vector of claim 3, wherein the gene of interest is an antibody gene.

9. The lentiviral vector containing two different genes linked together by an internal ribosome entry site (IRES).

* * * * *